United States Patent [19]

Frank et al.

[11] 4,194,063

[45] Mar. 18, 1980

[54] METHOD, COMPOSITION AND ELEMENTS FOR THE DETECTING OF NITROGEN-CONTAINING COMPOUNDS

[75] Inventors: David S. Frank; Ignazio S. Ponticello, both of Rochester, N.Y.

[73] Assignee: Eastman Kodak Company, Rochester, N.Y.

[21] Appl. No.: 880,827

[22] Filed: Feb. 24, 1978

[51] Int. Cl.$^2$ .............................................. G01N 33/14
[52] U.S. Cl. .......................................... 435/12; 435/4
[58] Field of Search ................. 195/103.5 R, 103.5 U; 23/230 B, 232 R

[56] References Cited

U.S. PATENT DOCUMENTS

| | | | |
|---|---|---|---|
| Re. 27,524 | 11/1972 | Nadeau | 195/103.5 |
| 3,145,086 | 8/1964 | Free | 23/253 |
| 3,806,416 | 4/1974 | Mollering et al. | 195/62 |
| 3,873,269 | 3/1975 | Kraffczyk et al. | 23/230 B |
| 3,992,158 | 11/1976 | Przybylowicz et al. | 23/253 TP |
| 4,125,377 | 11/1978 | Gindler | 23/230 B |

OTHER PUBLICATIONS

Hantzsch, Ann. Chem. Liebigs, 215, p. 1, 1882 (translation of pp. 5–8, only).
Knoevenagel, Annalen, 281, p. 25, 1894 (translation of pp. 25–28, only).
Dunsbach in Chemical Abstracts, vol. 66 (1967) 82993a.

*Primary Examiner*—Lionel M. Shapiro
*Attorney, Agent, or Firm*—Dana M. Schmidt

[57] ABSTRACT

Methods, compositions and elements for detecting a nitrogen-containing compound capable of releasing ammonia upon enzymatic action are described. The method comprises contacting in an aqueous medium a sample suspected of containing such a compound and a novel assay composition comprising at least one enzyme which catalyzes the decomposition of the compound to ammonia and detecting the ammonia by condensation with a β-diketone in the presence of an aldehyde, preferably formaldehyde, and measuring the color or fluorescence produced by any resulting dihydropyridine. According to a preferred embodiment, the aldehyde is generated in situ and the β-diketone is polymeric.

The foregoing assay composition can be incorporated into single-layer or multilayer analytical elements of the type known in the prior art. A preferred such element comprises an isotropically porous spreading layer in fluid contact with a reagent layer. The spreading layer is most preferably non-fibrous.

47 Claims, No Drawings

METHOD, COMPOSITION AND ELEMENTS FOR THE DETECTING OF NITROGEN-CONTAINING COMPOUNDS

BACKGROUND OF THE INVENTION

1. Field of the Invention

The present invention relates to novel methods, compositions, and elements for detecting nitrogen containing compounds capable of releasing ammonia upon enzymatic action.

2. Description of Related Art

There are several standard methods for the determination of urea. The Berthelot reaction utilizes the conversion of urea to ammonium carbonate by the action of urease followed by an oxidative condensation of ammonia with phenol catalyzed by sodium nitroprusside to form a blue indophenol. The condensation of diacetyl (or an oxime thereof) with urea in an acidic solution may be employed to produce a yellow diazine. In the Nesslerization procedure, urea is hydrolyzed by urease as in the Berthelot reaction and the ammonia produced is reacted with mercuric iodide and potassium iodide to yield (presumably) $NH_2Hg_2I_3$ (red). A titrimetric procedure may be used in which urea is hydrolyzed by urease and the ammonia titrated with HCl to a Bromcresol green-methyl red endpoint. Urea concentration may also be determined potentiometrically by the immersion of an $NH_4^+$ sensitive electrode in a solution containing urea and urease. Finally the ammonia produced by the action of urease upon urea may be coupled with α-ketoglutaric acid in the presence of L-Glutamate:NAD oxoreductase (deaminating), E.C. 1.4.1.2. and nicotinamide adenine dinucleotide, reduced form, to yield L-glutamate and the oxidized form of the coenzyme. The reaction is followed at 340 nm.

The condensation reaction involving two equivalents of a β-diketone and one each of ammonia and formaldehyde was first described by A. Hantzsch, *Ann. Chem. Liebigs*, 215, 1(1882). Its only clinical usage has apparently been in the detection of glycerides in which liberated glycerol is oxidized to formaldehyde and condensed with 2,4-pentanedione and an ammonium salt to yield the tetra-substituted dihydropyridine. This procedure was reported by F. Dunsbach, *Z. Klin. Chem.*, 4, 262 (1966) (N.B. CA 66:82993a). No suggestion is made to use this reaction to detect analyte other than formaldehyde.

The condensation reaction involving one equivalent of a β-diketone and one of ammonia was described by E. Knoevenagel, Annalen, 281, 25 (1894). No suggestion is made of using this reaction to detect analyte other than ammonia.

U.S. Pat. No. Re 27,524 reissued Nov. 28, 1972 describes a process for measuring the amount of a nitrogen-containing compound in a sample, the enzyme being reactive with the nitrogen-containing compound which process comprises:

(1) mixing the sample with a compound that is enzymatically reactive with ammonia;

(2) adding to the nitrogen-containing compound an amount of enzyme sufficient to release ammonia at a measurable rate; and (3) measuring the rate of reaction of ammonia with the compound that is enzymatically reactive with ammonia. The only compound reactive with ammonia which is specifically disclosed is β-nicotinamide-adenine dinucleotide.

Creatinine has been detected as described in U.S. Pat. No. 3,806,416 issued Apr. 23, 1974 by converting creatinine to creatine using creatinine amidohydrolase and subsequently converting creatine to sarcosine and urea using creatine amidinohydrolase. As described below, this pair of reactions can be coupled to the instant urea assay to provide an assay for creatinine.

U.S. Pat. No. 3,992,158 issued Nov. 16, 1976 to Przybylowicz and Millikan describes unique integral elements for use in the qualitative and quantitative analysis of liquids such as blood serum and urine, which elements preferably comprise a porous spreading layer in fluid contact or communication with a reagent layer which comprises at least one material interactive with a component or decomposition product of a component of the liquid. This patent does not describe specifically compositions of the type described herein.

U.S. Pat. No. 3,145,086 describes a diagnostic composition for the determination of abnormally high blood urea, preferably impregnated on a cellulose strip, which composition combines urease with an indicator system including a buffer and an indicator material capable of changing color in the presence of a pH change. There is no suggestion of the use of urease in combination with a β-diketone capable of condensing with ammonia and formaldehyde.

U.S. Pat. No. 3,873,269 describes a diagnostic composition for the determination of urea, preferably impregnated on an absorbent carrier such as filter paper, which combines urease with an indicator system capable of changing color in the presence of a pH change. There is no suggestion of the use of urease in combination with a β-diketone capable of condensing with ammonia in the presence of formaldehyde.

Commonly-owned U.S. application Ser. No. 688,446 filed on May 20, 1976, U.S. Pat. No. 4,066,403, issued Jan. 3, 1978 entitled "Improved Multilayer Analytical Element" by B. Bruschi, describes a dry element having at least two reagents for generating a measurable indication of the presence of BUN, and a barrier composition separating the two reagents, the composition being selectively permeable to a decomposition product which will react with one of the reagents. Nowhere is there a specific disclosure that diketones should be one of the reagents.

RELATED APPLICATIONS

Commonly-owned application U.S. Ser. No. 880,828 filed on Feb. 24, 1978, by J. Figueras et al entitled "Method, Composition and Element for the Detection of Nitrogen-Containing Compounds" discloses contacting in an aqueous medium a sample and a novel composition comprising an enzyme which catalyzes the decomposition of any nitrogen-containing compound to ammonia, and detecting the ammonia by condensation with a diketone. Nothing is stated about the advantages of using formaldehyde.

SUMMARY OF THE INVENTION

The compositions and elements of the present invention provide a means for detecting nitrogen-containing compounds via the formation of substituted or unsubstituted dihydropyridines. The reagents may be used in the form of aqueous solutions, reconstitutable powders or dry, single or preferably multilayer analytical elements.

As used herein, the term analyte refers to nitrogen-containing material which releases ammonia either directly on interaction with one or more enzymes or indirectly by the action of two or more enzymes which act sequentially on the analyte and on at least one decomposition product of the analyte.

According to the present invention, the ammonia may be present in a sample solution as ammonia or obtained in situ from analyte present in the solution sample by any of a variety of known enzyme catalyzed decompositions which result in the formation of ammonia. The ammonia is condensed with an appropriate β-diketone in the presence of an aldehyde, preferably formaldehyde, most preferably formaldehyde is generated in situ from a formaldehyde source, to produce a photometrically detectable substituted dihydropyridine whose concentration can be related to the concentration of nitrogen-containing analyte present in the sample. The assay may be performed kinetically.

If used as a multilayer element, the invention comprises at least one enzyme which catalyzes the decomposition of the analyte to $NH_3$, and a composition which forms a substituted or unsubstituted dihydropyridine in a reaction with said ammonia.

A preferred dry multilayer analytical element described herein comprises a spreading layer in fluid contact with a reagent layer. The various reactive materials are disposed within the element so that ammonia released by the action of at least one enzyme on analyte present within a liquid sample applied to the surface of the element is condensed with the β-diketone in the presence of formaldehyde. Optionally, the element may include a support.

The analyte-decomposing/ammonia-generating enzyme(s) and formaldehyde or formaldehyde source are preferably incorporated into the element as follows:
(a) all in the reagent layer;
(b) all in the spreading layer with the underlying layer serving as a registration or indicator receiving layer;
(c) the enzyme(s) in the spreading layer and the formaldehyde source in the reagent layer; or
(d) the formaldehyde source in the spreading layer and the enzyme(s) in the reagent layer.

The β-diketone is preferably incorporated into the reagent layer as described hereinafter.

DESCRIPTION OF PREFERRED EMBODIMENTS

The present invention involves novel methods, compositions and elements for detecting nitrogen-containing analyte capable of releasing ammonia upon enzymatic action in biological or other complex aqueous fluids. The procedure in simplified form may also be used for the detection of ammonia or ammonium ion.

Although the disclosure herein will be directed primarily to the determination of urea as analyte using urease as the enzyme which releases ammonia from the analyte, it should be apparent that numerous other analytes may be similarly determined. For example, creatinine can be determined using the methods and compositions described herein when the creatinine decomposition reactions are those described, for example, in U.S. Pat. Nos. 3,806,416, 3,907,644 and 3,912,588 wherein the nitrogen-containing creatinine is converted to urea by the following reactions:

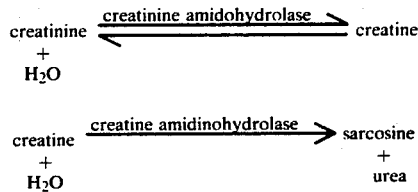

The urea is then determined by the method described herein.

Table I provides a listing of other nitrogen-containing compounds that can be determined by the procedure of this invention and enzymes which can be used in the ammonia-releasing reaction. After determining specific optimum conditions of temperature, ionic strength, etc., and a linear portion in a curve is obtained by plotting the rate of change in color formation or fluorescence versus nitrogen concentration, the procedures for all the determinations become identical and could be readily understood by reference to the examples presented herein.

Table I

| Parent compound | Enzyme |
| --- | --- |
| l-Lysine | l-Lysine amino acid oxidase |
| l-Histidine | Histidine-a-deaminase |
| l-Serine | l-Serine dehydrase |
| l-Threonine | l-Threonine amino acid oxidase |
| l-Homoserine | l-Homoserine amino acid oxidase |
| l-Cysteine | l-Cysteine amino acid oxidase |
| Glycine | Glycine oxidase |
| l-Aspartic acid | l-Aspartase |
| Quinine | Quinine deaminase |
| Aliphatic amines | Monoamine oxidase |
| d-Amino acids | d-Amino acid oxidase |
| l-Glutamine | l-Glutaminase |

The general chemical reactions in a total process of this invention are as follows:

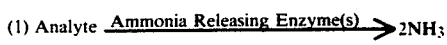

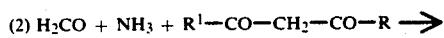

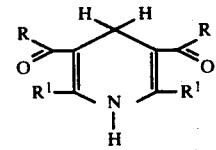

Wherein R and $R^1$ are as defined hereinafter. Equation (1) presents the decomposition of analyte to ammonia in the presence of a suitable enzyme. Reaction (2) shows the condensation of two equivalents of a β-diketone with one equivalent of ammonia and one equivalent of formaldehyde to form a dihydropyridine. Typically, the formaldehyde is formed in situ from a formaldehyde source such as Tris Nitro ® as described hereinafter.

This reaction sequence is an extended adaptation of the Hantzsch pyridine synthesis (A. Hantzsch, *Ann. Chem. Liebigs*, 125, 1 (1882)).

In the determination of urea reaction (1) would be

The formation of the condensation product can be monitored spectrophotometrically or spectrofluorimetrically to give a measure of the ammonia consumed in equation (2) and, therefore, a measure of the nitrogen and consequently the analyte present in the original sample. The wavelength of absorption and emission of the product is dependent on the structure of the dihydropyridine formed and consequently the β-diketone used in the reaction sequence chosen.

The urea assay described herein can, for the convenience of the user, be utilized in different physical formats. The reagents can be prepared as an aqueous solution and used to determine the analyte content of a sample immediately on hand. In addition, these solutions can be divided into quantities convenient for the user, freeze-dried according to conventional techniques, and stored for later reconstitution and use. In a further, preferred embodiment, a "dry" single or multi-layer analytical element can be prepared containing, in one or more layers, optionally on a support, all the reactants required for the determinations described herein. Analytical elements of these types which include "bibulous" materials impregnated or otherwise incorporating reagents, and so-called integral multi-layer elements which include layers to meter, spread, filter, etc. sample applied thereto are well known in the art.

Each of the above formats provides an accurate, convenient method for the assay of nitrogen-containing analyte using the formation of a dihydropyridine detectable by spectrophotometric or spectrofluorimetric techniques from a β-diketone, formaldehyde, and the ammonia released by the sample when contacted with appropriate enzyme(s).

SOLUTION ASSAY

The use of the reaction sequence described hereinabove in a solution assay employs techniques commonly known in the art. The necessary reagents are described hereinbelow:

The enzyme urea amidohydrolase (E.C. 3.5.1.5), commonly termed urease, is a highly specific enzyme catalyzing the decomposition of urea to ammonia. The enzyme may be obtained from bacterial sources such as *B. pasteurii* or from jack bean. The optimum pH of the enzyme varies from about 6.0 to 7.0 depending on the source. Urease is highly stable unless too highly purified, and has a useful life of about 12 months when stored at 4° C. Activity for urease is generally stated in Sumner Units (SU) where one SU of urease activity is that quantity of urease which will form 1 mg of ammonia nitrogen from urea in phosphate buffer, pH 7.0 at 20° C. in 5 minutes. The concentration of urease in the solution assay should be sufficiently high to rapidly convert the urea available in a given sample to ammonia. Activities of urease from about 100 $SU/_1$ to about 1000 $SU/_1$ are practical.

The carbon dioxide formed in the initial reaction is not further required for the determination of the urea and does not interfere in any way with the reactions involved in the total process.

In the determination of other analytes, as described hereinabove, other ammonia releasing enzyme(s) are substituted for the urease and the useful concentrations, pH optima, etc., therefore are readily determinable by the skilled artisan.

The formaldehyde required for reaction (2) is preferably obtained in situ from such commercially available formaldehyde sources as 2-(hydroxymethyl)-2-nitro-1,3-propanediol (Tris Nitro ® commercially available from Commercial Solvents Corp.) or a tetrahydro-oxazole such as Oxazolidine A ®, Oxazolidine E ®, or Oxazolidine T ® sold by Commercial Solvents Corporation.

The level of the formaldehyde source should be sufficient to provide all formaldehyde required for reaction with the ammonia released from the analyte. This requirement is generally fulfilled in the determination of urea in blood serum by concentrations of a formaldehyde source in the range of from about 0.5 to about 5 weight percent of the assay reagents and preferably in the range from about 1 to about 3 weight percent.

The β-diketone used in reaction (2) may be either a compound of the structure $R-CO-CH_2-CO-R^1$ wherein R is an aryl group having from about 6 to about 20 carbon atoms, a straight- or branched-chain alkyl, alkoxy or aralkyl group having from about 1 to about 20 carbon atoms, a cycloalkyl group of about 5 to about 7 carbon atoms or the atoms necessary to complete a recurring unit in a polymer backbone, and $R^1$ is alkoxy, amino, alkyl, cycloalkyl or aryl, or a polymer comprising a polymerized monomer having the formula:

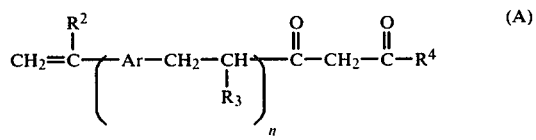

wherein n is 0 or 1, $R^2$ is hydrogen or methyl, Ar is arylene, preferably of from 6 to 12 carbon atoms, e.g., phenylene, naphthalene, including substituted phenylene or naphthalene, if desired, with alkyl or alkoxy groups preferably of from 1 to 10 carbon atoms as exemplified by methyl, ethyl, propyl, butyl, pentyl, hexyl, heptyl, octyl, nonyl, decyl, and isomers thereof, methoxy, ethoxy, propoxy, butoxy, pentoxy, etc., and cycloalkyl, preferably of from 5 to 7 carbon atoms, such as; for example, cyclopentyl, cyclohexyl, or cycloheptyl; cyano halide, such as bromide, chloride, fluoride, and iodide; and others known to those skilled in the art, and $R_3$ is hydrogen, aryl, alkyl or cycloalkyl and $R_4$ is alkyl including cycloalkyl and substituted alkyl and cycloalkyl, having from 1 to 20 carbon atoms as exemplified by methyl, ethyl, propyl, butyl, pentyl, hexyl, heptyl, octyl, nonyl, decyl, benzyl, cyclopentyl, cyclohexyl, cycloheptyl, and isomers thereof; or aryl preferably of from 6 to 12 carbon atoms, e.g., phenyl, naphthyl, unsubstituted or substituted with alkyl, carboxyl, alkoxycarbonyl and the like, e.g., tolyl, xylyl, etc.

Monomers of the structure (A) can be reacted with themselves to form homopolymers, or can be reacted with from about 0 to about 99% by weight of at least one other ethylenically unsaturated monomer to form a polymeric substance. Polymers of this type are not commercially available, hence some discussion of their properties, preparation, etc. is required herein.

The molecular weights of such polymers are subject to wide variation, but are often in the range of about 5000 to about 3,000,000. These polymers, which are generally water soluble, preferably have inherent viscosities (0.25 g polymer in 100 ml 1 N. sodium chloride at 25° C.) from 0.10 to 2.0, more preferably from about 0.25 to about 1.25.

Polymers included in this definition are homopolymers or interpolymers of a first polymerized monomer with a second polymerized monomer, the first polymerized monomer having repeating units of formula (A) defined above.

A particularly useful monomer group according to this invention is 6-(m- and p-vinylphenyl)-2,4-hexanedione. The latter is a mixture of the meta (60 percent, by weight) and para (40 percent) isomers of the substituted aryl which are not easily separated. Little difference in behavior in polymerization between the mixture and the pure isomers is observed.

These two monomers can be polymerized to advantage with one or more monomers as shown in the following preferred polymers: a copolymer of 6-(m- and p-vinylphenyl)-2,4-hexanedione (20–80 weight percent) and sodium 3-methacryloyloxypropane-1-sulfonate (80–20 weight percent); a copolymer of 6-(m- and p-vinylphenyl)-2,4-hexanedione (20–80 weight percent) and sodium p-styrene sulfonate (80–20 weight percent); and a copolymer of 6-(m- and p-vinylphenyl)-2,4-hexanedione (20–80 weight percent) and sodium 2-acrylamido-2-methylpropane-1-sulfonate (80–20 weight percent).

The preparation of 6-(m- and p-vinylphenyl)-2,4-hexanedione follows procedures as described by C. R. Hauser and T. M. Harris, *J. Amer. Chem. Soc.*, 80, 6360 (1958); and L. Weiler, *J. Amer. Chem. Soc.*, 92, 6702 (1970).

As noted above, useful polymers can comprise at least one additional polymerized ethylenically unsaturated monomer. Exemplary monomers are: vinyl esters, amides, nitriles, ketones, halides, ethers, alpha-beta unsaturated acids or esters thereof, olefins, diolefins and the like, as exemplified by acrylonitrile, methacrylonitrile, styrene, alpha-methyl styrene, sodium p-styrenesulfonate, acrylamide, methacrylamide, vinyl chloride, methyl vinyl ketone, fumaric, maleic and itaconic esters, 2-chloroethyl vinyl ether, acrylic acid, sodium methacryloyloxyethyl sulfate, sodium 3-methyl-1-vinylimidazolium methosulfate, 1,2-dimethyl-5-vinylpyridinium methosulfate, methacrylic acid, dimethylaminoethyl methacrylate, 4,4,9-trimethyl-8-oxo-7-oxa-4-azonia-9-decene-1-sulfonate, N-vinylsuccinamide, N,N-dimethyl-N-2-hydroxypropylamine methacrylimide, N-vinylphthalimide, N-vinylpyrrolidone, butadiene, isoprene, vinylidene chloride, ethylene and the like. Sulfoalkylacrylate and sulfoalkylacrylamide salts are particularly useful as comonomers in the practice of this invention. Examples of such salts are sodium 2-acrylamido-2-methylpropane-1-sulfonate, sodium 3-methacryloyloxypropane-1-sulfonate, sodium 3-acryloyloxypropane-1-sulfonate, sodium 4-acryloyloxybutane-2-sulfonate, and others as described in Dykstra, U.S. Pat. No. 3,411,911 issued Nov. 19, 1968.

When the polymer contains up to 30% by weight of one or more of the monomers containing active methylene groups, the polymerization can usually be carried out as a solution polymerization in a suitable medium, for example, water or mixtures of water with water miscible solvents, as exemplified by methanol, ethanol, propanol, isopropanol, and the like. When the polymer contains more than 30% by weight of one or more monomers containing active methylene groups, the polymerization can usually be carried out by solution polymerization in a suitable organic solvent, for example, acetone, benzene, cyclohexanone, N,N-dimethylformamide, dimethyl sulfoxide, tetrahydrofuran, and the like; or by aqueous emulsion or suspension polymerization according to methods well known to those skilled in the art.

The temperature at which the polymers described herein are prepared is subject to wide variation since this temperature depends upon such variable features as the specific monomer used, duration of heating, pressure employed and like considerations. However, the polymerization temperature generally does not exceed about 110° C., and most often it is in the range of about 50° to about 100° C.

The pressure employed in the polymerization is usually only sufficient to maintain the reaction mixture in liquid form, although either superatmospheric or subatmospheric pressures can be used where such use is advantageous. The concentration of polymerizable monomer in the polymerization mixture can be varied widely with concentrations up to about 100%, by weight, and preferably about 10 to about 70%, by weight, based on the weight of the polymerization mixture, being satisfactory. Suitable catalysts for the polymerization reaction include, for example, free radical catalysts, such as hydrogen peroxide, cumene hydroperoxide, water soluble azo type initiators and the like. In redox polymerization systems conventional ingredients can be employed. If desired, the polymer can be isolated from the reaction vehicle by freezing, salting out, precipitation or any other procedure suitable for this purpose.

As indicated in U.S. Pat. No. 3,142,568, issued July 28, 1964, it is sometimes advantageous to include a surface active agent or compatible mixtures of such agents in the preparation of vinyl or addition polymers. Suitable wetting agents include the nonionic, ionic and amphoteric types as exemplified by the polyoxyalkylene derivatives, amphoteric amino acid dispersing agents, including sulfobetaines and the like. Such wetting agents are disclosed in U.S. Pat. No. 2,600,831 issued June 17, 1952; U.S. Pat. No. 2,271,623 issued Feb. 3, 1942; U.S. Pat. No. 2,275,727 issued Mar. 10, 1942 and U.S. Pat. No. 2,787,604 issued Apr. 2, 1957; U.S. Pat. No. 2,816,920 issued Dec. 17, 1957; and U.S. Pat. No. 2,739,891 issued Mar. 27, 1956. Further information on such polymer compounds may be obtained from U.S. Pat. No. 4,011,201 by I. S. Ponticello, issued Mar. 8, 1977.

The β-diketone should be chemically pure and is preferably used at a concentration of from about 0.5 to about 5 weight percent of the reagent composition and preferably from about 1 to about 3 weight percent.

The total process occurs readily in either base or acid buffered systems. When a base buffer system is employed, about 0.5 to about 2.5 weight percent of a buffer such as tris(hydroxymethyl)aminomethane, 5,5-diethyl barbituric acid, boric acid or the like is added followed by adjustment of pH with an acid such as hydrochloric acid to a pH of from about 7.5 to about 9.5 and preferably from about 8.3 to about 8.8.

When an acid buffer system is employed, about 0.5 to about 2.5 weight percent of a buffer such as acetic acid, citric acid or the like is added followed by adjustment of pH with a base such as sodium hydroxide to a pH of from about 4.5 to about 6.5 and preferably from about 5.9 to about 6.2. The acid buffered system has the advantage of operating within the optimum pH range of the enzyme urease.

In use the nitrogen-containing analyte is detected by contacting in an aqueous medium a liquid suspected of containing the analyte and a reagent composition comprising enzyme or enzymes which catalyze the release of ammonia from the analyte, β-diketone and formaldehyde or a formaldehyde source for a period sufficient to obtain color or fluorescence formation from which a rate of endpoint determination of ammonia concentration and consequently analyte concentration can be made. In the assay of blood serum for urea the unknown sample and the reagent composition are preferably contacted at a temperature of between about 37° and about 60° C. for up to about 5 minutes. In such a determination a preferred volume ratio of test sample to reagent solution is from about 1:5 to about 1:50.

RECONSTITUTABLE POWDER

By selection of an appropriate formaldehyde source such as a solid oxazolidine, the assay composition may be easily prepared as a water reconstitutable powder. The techniques for freeze-drying and reconstituting enzymes are well known in the art. Reconstitutable powders provide the advantage that large quantities of the reagents may be prepared and used as required. Operator time and solution preparation errors are minimized.

ANALYTICAL ELEMENTS

The preferred analytical elements of the present invention simplify greatly the assay of liquids for nitrogen-containing analyte. Using these elements such an assay requires no reagent mixing and can be automated to permit rapid determination of nitrogen-containing analyte with a minimum of laboratory technician participation.

Thus, according to a preferred embodiment of the present invention the foregoing reagents are incorporated into an integral element for the detection of nitrogen-containing analyte in aqueous liquids. The element comprises a spreading layer in fluid contact with a reagent layer and contains interactive materials comprising:

(a) enzymes which catalyze the release of ammonia from nitrogen-containing analyte; and (b) an ammonia detection composition comprising
 (1) formaldehyde or a formaldehyde source, and
 (2) a β-diketone which can condense with ammonia and (1) to form a dihydropyridine.

The interactive materials are disposed within the element so that a nitrogen-containing analyte in a liquid sample applied to the element releases ammonia to produce, in the element, a detectable change that is related, preferably quantitatively, to the analyte content of the liquid sample. Optionally, the element may include a support.

Other than the β-diketone, which is always most preferred in the reagent layer, the interactive materials which accomplish release of ammonia and ammonia detection are preferably incorporated into the element as follows:

(I) all in the reagent layer;
(II) all in the spreading layer;
(III) the enzyme(s) in the spreading layer and the formaldehyde source in the reagent layer; or
(IV) the formaldehyde source in the spreading layer and the enzyme(s) in the reagent layer.

The analytical elements described herein will be referred to primarily as elements for the determination of urea and nitrogen-containing analyte, however, it should be clear that they are similarly useful for the determination of enzymes which release ammonia from a substrate and for ammonia per se.

Integral analytical elements having a spreading layer and a reagent layer are described in U.S. Pat. No. 3,992,158 issued Nov. 16, 1976 in the names of E. P. Przybylowicz and A. G. Millikan.

The preferred elements described herein are of this type and comprise:

(1) a spreading layer which serves to deliver a uniform apparent concentration of analyte to;
(2) a reagent layer in fluid contact with the spreading layer; and
(3) optionally, a support.

The various enzymes which serve to release ammonia from an analyte contained in a liquid sample applied to the spreading layer and other interactive materials which provide detectable changes related to the analyte content of the liquid, are incorporated into one or more layers of the element.

Reference herein to fluid contact between a spreading layer and a reagent layer in an integral analytical element identifies the ability of a fluid, whether liquid or gaseous, to pass in such element between superposed regions of the spreading layer and the reagent layer. Stated in another manner, fluid contact refers to the ability to transport components of a fluid between the layers in fluid contact. Although such layers in fluid contact can be contiguous, they may also be separated by intervening layers as described hereinafter. However, layers in the element that physically intervene a spreading layer and reagent layer in mutual fluid contact will not prevent the passage of fluid between the fluid contacting spreading and reagent layers.

THE SPREADING LAYER

As used herein, the term spreading layer refers to a layer, isotropically porous or otherwise, that can accept a liquid sample, whether applied directly to the spreading layer or provided to it from a layer or layers in fluid contact with the spreading layer, and which distribute (i.e., meters) within the layer the solvent or dispersion medium of the sample and at least one dissolved or dispersed component such that a uniform concentration of such component is provided at the surface of the spreading layer facing the reagent layer(s) of the element. It should be understood that the uniformity of such concentration is a uniformity as measured by techniques such as those described hereinafter. As such, the uniform concentration can also be termed a uniform apparent concentration. (The spreading layer is synonymously referred to herein as the metering layer.) In the context of this invention, the spread component will, of course, include analyte present in the applied sample. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The spreading layer can be an isotropically porous layer. Reference herein to isotropic porosity identifies the fact of substantial porosity in all directions within the spreading layer. It will be understood that the degree of such porosity may be variable, if necessary or desirable, for example, regarding pore size, percentage of void volume or otherwise. It shall be understood that the term isotropic porosity (or isotropically porous) as used herein should not be confused with the terms iso-porous or ionotropic often used with reference to filter membranes to signify those membranes having pores that are continuous between membrane surfaces. Likewise, isotropic porosity should not be confused with the term isotropic, used in contradistinction to the term anisotropic, which signifies filter membranes having a thin "skin" along at least one surface of the membrane. See, for example, *Membrane Science and Technology*, James Flinn Ed, Plenum Press, New York (1970).

As will be appreciated, the extent of spreading is dependent in part on the volume of liquid to be spread. However, it should be emphasized that the uniform apparent concentration obtained with spreading is substantially independent of liquid sample volume and will occur irrespective of the extent of spreading. As a result, elements of this invention generally do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g., one square centimeter), there is no need to remove excess moisture from the element after application of a liquid sample. Further, because spreading occurs in the spreading layer and the spread component is provided to the fluid contacting reagent layer without apparent substantial lateral hydrostatic pressure, there is not the "ringing" problem often seen with prior analytical elements when soluble reagents were used.

The spreading layer need only produce a uniform concentration of spread component per unit area at its surface facing a reagent layer with which the spreading layer is in fluid contact, and it is very convenient to determine whether a particular layer can be suitable for spreading purposes by means of the simple test described in the aforementioned Przybylowicz and Millikan U.S. Pat. No. 3,992,158.

Useful materials and methods for preparing spreading layers are described in detail in aforementioned U.S. Pat. No. 3,993,158 which is expressly incorporated herein by reference.

THE REAGENT LAYER(S)

Reagent layer(s) in the elements of this invention are desirably permeable, preferably uniformly permeable, and optionally porous if appropriate, to components spreadable within the metering or spreading layer. As used herein, the term permeability includes permeability arising from porosity, ability to swell or any other characteristic. Such layers generally include a matrix in which is distributed, i.e., dissolved or dispersed, the enzymes and other reagents interactive with analyte or decomposition products of analyte and ammonia. Interactive materials are discussed hereinafter.

The distribution of interactive materials (i.e., enzymes and other reagents) can be obtained by dissolving or dispersing them in the matrix material. Although uniform distribution of interactive materials are often preferred, they may not be necessary if the interactive material is, for example, an enzyme which is not consumed in any reaction but only serves as a catalyst which is continuously reused.

Desirably, reagent layers are uniformly permeable to spread components. Uniform permeability of a layer refers to permeability such that, when a homogeneous fluid is provided uniformly to a surface of the layer, measurements of the concentration of such fluid within the layer, made with identical equipment and under identical conditions but through different regions of a surface of the layer, will yield (i.e., be capable of yielding) substantially equal results. By virtue of uniform permeability, undesirable concentration gradients within, for example, a reagent layer as described herein, are avoided.

The choice of a matrix material for the reagent or registration layers described herein is, of course, variable and dependent on the intended method of use of the element as well as the particular interactive materials which are incorporated therein as described hereinafter. Desirable matrix materials can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Organophilic materials such as cellulose esters and the like can also be useful, and the choice of materials in any instance will reflect the use parameters for any particular element. For example, if a reagent which degrades gelatin is used, gelatin is not a particularly suitable reagent matrix. To enhance permeability of the reagent layer, if not porous, it is often useful to use a matrix material that is moderately swellable in the solvent or dispersion medium of liquid under analysis.

In addition to its permeability, the reagent layer is desirably substantially free from any characteristic that might appear as or contribute to mottle or noise in the detection of an analytical result produced in an integral element of the invention. For example, variations in color or in texture within the reagent layer, as may occur when fibrous materials such as papers are used as a permeable medium, may be disadvantageous due to non-uniform reflectance or transmittance of detecting energy, e.g., when the detectable change has occurred in and is detected in the reagent layer. Also, although fibrous materials like filter and other papers are highly permeable overall, they typically exhibit widely ranging degrees of permeability between regions of the paper, for example, based on structural variations such as fiber dimensions and spacing. As a result, such materials are not considered uniformly permeable and, as such, although useful, are not preferred in either the spreading or reagent layers of the preferred embodiments of the present invention. It should be appreciated that the use of fibrous constituents, such as in appropriate combination with the non-fibrous materials, may be desirable.

INTERACTIVE MATERIALS

The enzymes and other interactive materials used in the elements of the present invention are described hereinabove.

The concentrations of the various interactive materials useful in the elements described herein are dependent to a large extent upon the concentration of analyte in the sample under test, the sophistication of the detection apparatus, the detectable product produced, etc., and are readily determinable by the skilled artisan. Typical values are shown in Table II and the examples below.

Table II below provides a ready reference for the generally useful and preferred concentration ranges of the various components of the novel assay compositions described herein.

Table II

| Interactive Material | Generally useful ranges | Preferred ranges |
| --- | --- | --- |
| Urease | 100–1000 su/l | 200–500 su/l |
| Diketone | 1–9 g/m$^2$ | 3–8 g/m$^2$ |
| Formaldehyde Source | .2–9 g/m$^2$ | .3–6 g/m$^2$ |

Of course useful results may be obtained outside of these ranges; however, these have generally been found useful and preferred in elements as described herein.

In the foregoing Table II, one summer unit of enzyme is defined as that quantity of enzyme which results in the conversion of one micromole of substrate in one minute at 37° C. and pH 7.

As is well recognized in the art, all enzymes possess a pH-activity profile, i.e., a graphic representation of variations in the activity of the enzyme with varying pH.

Thus, it is readily apparent that it is generally desirable to buffer the layer(s) of the elements described herein which contain the respective reagents at pH levels which optimize the activity of contained enzymes. Techniques for achieving this type of buffering are well known in the art and involve dissolving or dispersing suitable concentrations of buffer in the compositions which are subsequently dried to form the layered element. Suitable buffers for buffering to preselected pH levels are described in detail by Good in *Biochemistry*, 5, 467 (1966). Particularly preferred buffers are discussed hereinabove.

SUPPORTS

The integral analytical elements of the present invention can be self-supporting or the spreading layer, reagent layer and any other associated layers can be coated on a support. Useful support materials, when such are used, include paper and polyolefin coated paper, as well as a variety of polymeric materials such as cellulose acetate, poly(ethylene terephthalate), polycarbonates and polyvinyl compounds such as polystyrenes, etc. The support can be opaque or it can transmit light or other energy depending, of course, on the mode of detection used. A support of choice in any case will be compatible with the intended mode of result detection. Preferred supports include transparent support materials capable of transmitting electromagnetic radiation of a wavelength within the region between about 200 nm and about 900 nm. The support need not, of course, transmit over the entire 200–900 nm region but must transmit in the region of the indicating radiations. When an element includes a support, the reagent layer is interposed in the element between the support and the spreading layer. Specifically preferred transmission ranges for elements of the present invention will be apparent from the discussion of the various preferred indicator compositions and examples discussed herein. When used, supports having thicknesses of between about 1 and about 10 mils have been found satisfactory, although the thickness can vary broadly depending on such factors, for example, as the intensity of the detecting radiation and the sensitivity of the detecting apparatus.

OTHER LAYERS

The element may incorporate a distinct registration layer which contains no reagents but receives dihydropyridine produced in the reagent or spreading layer and holds it for detection.

The analytical element of the present invention is preferably adapted for use in an analytical system employing reflection techniques of spectrophotometric or spectrofluorometric analysis, and consequently generally includes a layer which functions as a reflecting layer and thereby provides a suitable background for measurement of detectable product through the support side of the element. The reflecting layer will permit the passage of analyte and/or decomposition products of analyte to the reagent layer, and should provide an effective background for reflection spectrophotometry. A white background is generally preferred for this purpose. In view of its function as a background for indicator formed in the reagent or registration layer, any reflective layer will normally intervene the spreading and reagent or registration layers. Such a layer may, however, intervene a reagent and registration layer where such structure is appropriate. Reflectance can be provided by a layer also serving, for example, as a spreading layer or it can be provided by an additional layer that may not have an additional function within the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

Filtering layers may also be present in the element. The composition and preparation of such layers are well known in the art and, when present, they serve to remove from the sample components which could interfere with the indicating reaction or otherwise hinder the determination. Thus, in the use of the multilayer analytical element for analysis of analyte in whole blood, a separate filtering layer could serve to remove red blood cells while transmitting the serum to the layer below. In the analysis of blood serum or other fluids, the filtering layer may serve to remove unwanted components which could hinder or confuse the primary indicating reaction. The aforementioned blush polymer layers may also, under certain circumstances, serve as filtering layers. If the element is to be used for analysis of whole blood, it is desirable that any filtering layer have a pore size of from about 0.5 to about 5 microns.

In elements of the type described herein, it is preferred to use the polymeric β-diketones defined hereinabove. These materials prevent loss of the β-diketones in the layered structure due to either evaporation or migration. Furthermore, certain of the polymeric β-diketones may serve as the binder for the reagent layer, thereby assuring compatibility of the diketone with the binder. Among the polymeric materials specifically preferred for this purpose are poly[6-(m- and p-vinylphenyl)-2,4-hexanedione-co-3-methacylyloxypropane-1-sulfonic acid, sodium salt](mole ratio 1:1), poly[6-(m- and p-vinylphenyl)-2,4-hexanedione-co-2-acrylamido-2-methylpropane-1-sulfonic acid, sodium salt](mole ratio 1:1), and poly[6-(m- and p-vinylphenyl)-2,4-hexanedione-co-sodium p-styrenesulfonate](mole ratio 1:1).

ELEMENT PREPARATION

In preparing integral analytical elements of this invention, the layers can be preformed separately and laminated to form the overall element. Layers prepared in such a manner are typically coated from solution or dispersion on a surface from which the dried layer can be physically stripped. However, a convenient method which can avoid the necessity for multiple stripping and lamination steps is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well known in the preparation of light-sensitive photographic films and papers. Interlayer adhesion problems can be overcome without harmful effect by means of surface treatments including extremely thin application(s) of subbing materials such as are used in photographic films. A more detailed description of methods for preparing elements of this type can be found in aforementioned U.S. Pat. No. 3,992,158.

The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers having a thickness of from about 5 microns to about 300 microns have been particularly useful, although wider variations in thickness are acceptable and may be desirable for particular elements.

When preparing an isotropically porous spreading layer, it is useful to have void volume comprise at least about 25% of the total layer volume, and void volumes of from 50-95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous "blush" polymers are used in the spreading layer. The void volume of any such layer can be calculated with reasonable accuracy by a variety of techniques such as the statistical method described in Chalkley, *Journal of the National Cancer Institute*, 4, 47 (1943) and by direct weighing and determining the ratio of actual weight of the layer to the weight of solid material equal in volume to that of the layer, comparably composed of constituents from the layer. It will be appreciated that the pore size in any case should be sufficient to permit spreading of analyte and decomposition products of analyte as may be appropriate in view of the location of the various interactive materials in the element.

For reagent layers, a coating solution or dispersion including the matrix and incorporated interactive materials can be prepared, coated as discussed herein and dried to form a dimensionally stable layer. The thickness of any reagent layer and its degree of permeability are widely variable and depend on actual usage. Dry thicknesses of from about 10 microns to about 100 microns have been found useful.

The ammonia releasing enzyme or enzymes can be incorporated into the reagent layer. However, according to a highly preferred embodiment of the present invention, such interactive material is incorporated into the spreading layer, for example, by dispersing the enzymes in a lyophilized state in the coating medium used to form the spreading layer, and then coating this mixture over the reagent layer. According to this embodiment, spreading of the sample and release of ammonia are accomplished substantially simultaneously and the ammonia transmitted to the reagent layer. Such a configuration utilizes the time needed to spread the sample to prepare it for immediate reaction with the ammonia detection reagents in the reagent layer. As another alternative, a distinct layer which includes the ammonia releasing enzyme or enzymes may be incorporated between the spreading layer and the reagent layer to accomplish ammonia release before the sample reaches the ammonia detection reagents but after spreading is complete.

Wherever the enzymatic ammonia-releasing material is incorporated, the layer should be buffered, if at all possible, to optimize the enzyme activity. In the case of an element for the detection of urea wherein urease is used as the ammonia releasing enzyme, the layer should be buffered at a pH of between about 4.8 and about 9.5. The pH optima for other ammonia releasing enzymes are, of course, readily determinable and layers containing same should be appropriately buffered.

A preferred embodiment of the integral elements hereof uses a reagent layer prepared by modifying an assay solution described hereinabove with a binder such as gelatin and solvent such as water and coating such a solution into a layer and drying. Such a layer comprises from about 40 to about 54 weight percent binder, from about 21 to about 32 weight percent of $\beta$-diketone, from about 18 to about 22 weight percent of formaldehyde source, from about 0.3 to about 0.4 weight percent urease and from about 3.5 to about 5.0 weight percent of buffer.

As all of the layers described herein are preferably formed by coating from solutions or dispersions as described in the aforementioned Przybylowicz and Millikan application, it is often necessary to include coating aids which impart uniform coating properties to the layers.

Whatever coating aids are used for this purpose it is important that they do not inhibit or interfere with any of the enzymes or reagents present in any of the various layers. Particularly useful coating aids include nonionic surfactants such as the octylphenoxy polyethoxy ethanols commercially available from Rohm and Haas Company under the Triton tradename (X-100, 102, 165, 305 and 405 being particularly useful), p-nonylphenoxy-(polyglycidol) commercially available from Olin Mathieson Corporation under the tradename Surfactant 10G, and polyethylene glycols such as the Carbowax materials available from Union Carbide. Of course, surfactants which are useful as hydrolysis stimulators may also serve as coating aids which improve the coating characteristics of the materials in manufacture. When used as coating aids, concentrations of surfactant on the order of between about 0.05 and about 10 percent by weight have been found useful. Preferred concentration ranges for surfactants as coating aids range between about 0.5 and about 2% by weight.

In addition to coating aids, the element may include small amounts of other addenda such as preservatives, e.g., ethylenediamine tetracetic acid (about 1% by weight) or dithithreitol (about 0.5% by weight), etc.

USE OF THE ELEMENT

In use, as demonstrated by the examples which follow, a sample usually on the order of from about 5 to about 50 μl is applied to the spreading or other outermost layer of the element. It is usually applied as a contact spot or free drop, using known application techniques and apparatus. In passage through the spreading layer the sample drop is spread and is then delivered to the underlying reagent layer. Also during passage through the spreading layer or the reagent layer, depending upon the embodiment used, analyte contained in the applied sample releases ammonia on contact with the appropriate enzyme(s) which ammonia is finally detected by measurement of increased levels of color or fluorescence. This increase in color or fluorescence can be quantified and related to the ammonia released and consequently the concentration of analyte in the sample. The measurement of absorbance of light at 412 nm or exciting the sample with light of 412 nm and detecting emissions at 490 nm have proven both practical and effective for some of the dihydropyridines useful with this invention.

The element can be held at a constant temperature in the range from about 30° to about 60° C. while monitoring the reaction. The assay method does not require complete reaction and can be done kinetically.

The following examples are included to illustrate further the present invention.

EXAMPLE 1

Detection of Ammonia

Aqueous ammonium sulfate (0.1 ml) of the indicated concentration was added to test tubes each containing aqueous solutions comprising 3 ml sodium borate buffer (0.1 M) pH 8.7 which contained 1% by volume acetylacetone and 0.1 ml 30% formaldehyde. The solutions were heated for 20 min. at 50° C. and the absorbance read at 412 nm using a 1 cm cell path length.

| Concentration of $[NH_4]_2SO_4(M)$ | Absorbance |
|---|---|
| 0.0 | 0.00 |
| 0.02 | .05 |
| 0.05 | .12 |
| 0.1 | .19 |
| 0.15 | .22 |
| 0.2 | .29 |

EXAMPLE 2

Aqueous ammonium sulfate (0.1 ml) of the indicated concentration was added to test tubes each containing aqueous solutions comprising 3 ml sodium barbitol buffer (0.2 M) pH 8.7 containing 1% by volume acetylacetone and 0.1 ml 30% Tris Nitro$^R$ [tris(hydroxymethyl)nitromethane]. The tubes were heated for ten minutes at 50° C. and absorbance read at 412 nm.

| Concentration of $[NH_4]_2SO_4(M)$ | Absorbance |
|---|---|
| 0 | .21 |
| .01 | .21 |
| .05 | .23 |
| .1 | .355 |
| .15 | .585 |
| .2 | .780 |

EXAMPLE 3

Solution Assay for Ammonia

Aqueous ammonium sulfate (0.1 ml) of the indicated concentration was added to test tubes each containing aqueous solutions of sodium barbitol buffer (0.2 M, 3 ml) at a pH of 8.0, a copolymer of 6-(m- and p-vinylphenyl)-2,4-hexanedione and 3-methacryloyloxypropane-1-sulfonic acid (1:1, 1% by weight) and Tris Nitro ® (30%, 0.1 ml) as a formaldehyde source.

The tubes were heated for 20 minutes at 50° C. and absorbance read at 412 nm.

| Concentration of $(NH_4)_2SO_4$, (M) | Absorbance |
|---|---|
| 0 | .000 |
| .01 | .112 |
| .10 | 1.22 |

EXAMPLE 4

Solution Assay for Urea

Aqueous urea (0.1 ml) of the indicated concentration was added to test tubes each containing aqueous solutions of sodium barbitol buffer (0.2 M, 3 ml), acetylacetone (1% by volume), Tris Nitro ® (0.100 ml) as formaldehyde source, and an aqueous extract of 250 mg Jack Beans (urease) in 5 ml of 0.1 M pH 7 sodium phosphate buffer (0.100 ml).

The tubes were heated for 20 minutes at 50° C. and absorbance measured at 412 nm. Blanks contain no urease.

| Concentration of Urea (M) | pH 8.0 Blank | pH 8.0 | pH 8.7 Blank | pH 8.7 |
|---|---|---|---|---|
| 0 | 0 | 0 | 0 | 0 |
| .02 | .01 | .045 | .065 | .03 |
| .04 | .013 | .125 | .045 | .20 |
| .067 | .0 | .245 | .065 | .41 |
| .1 | .02 | .395 | .065 | .54 |

EXAMPLE 5

An element comprising a transparent polymeric support coated with two layers, the first comprising 6.5 g/m$^2$ Tris nitro$^R$, 8.0 g/m$^2$ gelatine, 13 g/m$^2$ of a 1:1 copolymer of 6-(m,p-vinylphenyl)-2,4-hexanedione and 3-methacryloyloxypropane-1-sulfonic acid, 0.4 g/m$^2$ ethylenediaminetetraacetic acid disodium salt, 400 Sumner units/m$^2$ urease 0.32 g/m$^2$ Poly(ethylene glycol), 0.05 g/m$^2$ potassium dihydrogen phosphate 0.3 g/m$^2$ disodium hydrogen phosphate and 0.03 g/m$^2$ bis(-vinylsulfonylmethyl) ether overcoated with a spreading layer comprising 7.8 g/m$^2$ cellulose acetate, 54.8 g/m$^2$ titanium dioxide, 1.6 g/m$^2$ polyurethane and 3.2 g/m$^2$ octylphenoxy polyethoxy ethanol was spotted with 0.010 ml portions of aqueous urea and incubated for 20 minutes at 37° C. and 10 minutes at 56.5° C. The yellow spots formed under the aqueous urea were read fluorimetrically with excitation at 430 nm and emission at 490 nm.

| Concentration of Urea (M) | Relative Fluorescence |
|---|---|
| 0 | 47 |
| 0.01 | 87 |
| 0.02 | 119 |
| 0.03 | 147 |
| 0.04 | 187 |

ALTERNATE EMBODIMENTS

As should be apparent to the skilled artisan, the reagent compositions described herein can also be incorporated into the myriad of analytical elements described in the art, including those using at least one "bibulous" layer which has been impregnated in one way or another with a reagent composition which produces a detectable change on contact with appropriate analyte. Elements of this kind incorporating reagent compositions as described herein are intended to be within the scope of the appended claims. Such elements are structurally described, for example, in the following U.S. Pat. Nos. 2,912,309, 3,092,465, 3,349,006, 3,099,605, 3,811,840, 3,881,993, 3,901,657, 3,552,928, 3,607,093, 3,798,004, 3,802,848.

The invention has been described in detail with particular reference to certain preferred embodiments thereof, but it will be understood that variations and modifications can be effected within the spirit and scope of the invention.

We claim:

1. An element for the determination of nitrogen-containing analyte in an aqueous sample, said element comprising at least one enzyme which catalyzes the decomposition of the analyte to ammonia, a $\beta$-diketone capable of forming a detectable dihydropyridine on condensation with ammonia in the presence of formaldehyde, and formaldehyde or a formaldehyde source.

2. The element of claim 1 wherein the $\beta$-diketone is selected from the group consisting of:
(a) compounds of the formula

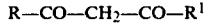

wherein R is an aryl group having from about 6 to about 20 carbon atoms, a straight- or branched-chain alkyl, alkoxy, or aralkyl group having up to about 20 carbon atoms, a cycloalkyl group of about 5 to about 7 carbon atoms or the atoms necessary to complete a recurring unit in a polymer backbone, and $R^1$ is alkyl, cycloalkyl, or aryl; and
(b) polymers comprising:
(I) from about 1 to about 100% by weight of a polymerized monomer having the formula:

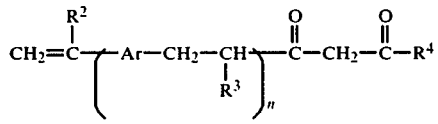

wherein n=0 or 1, $R^2$ is hydrogen or methyl, $R^3$ is hydrogen, alkyl, aryl or cycloalkyl, Ar is arylene, $R^4$ is alkyl or aryl; and (II) from about 0 to about 99% by weight of at least one ethylenically unsaturated monomer.

3. An element for the determination of nitrogen-containing analyte in an aqueous sample, said element comprising, in fluid contact, an isotropically porous spreading layer and a reagent layer, and including a $\beta$-diketone and formaldehyde or a formaldehyde source and at least one enzyme which catalyzes the decomposition of the analyte to ammonia.

4. The element of claim 3 wherein the $\beta$-diketone is selected from the group consisting of:
(a) compounds of the formula

wherein R is an aryl group having from about 6 to about 20 carbon atoms, a straight- or branched-chain alkyl, alkoxy, or aralkyl group having up to about 20 carbon atoms, a cycloalkyl group of about 5 to about 7 carbon atoms or the atoms necessary to complete a recurring unit in a polymer backbone and $R^1$ is alkyl, cycloalkyl, or aryl; and
(b) polymers comprising:
(I) from about 1 to about 100% by weight of a polymerized monomer having the formula:

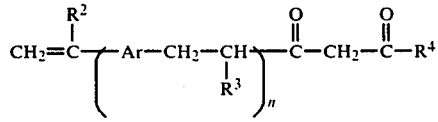

wherein n=0 or 1, $R^2$ is hydrogen or methyl, $R^3$ is hydrogen, alkyl, aryl or cycloalkyl, Ar is arylene, $R^4$ is alkyl or aryl; and
(II) from about 0 to about 99% by weight of at least one ethylenically unsaturated monomer.

5. The element of claim 3 wherein the layer containing the enzyme is buffered to a pH of between about 4.5 and about 9.5.

6. The element of claim 3 wherein said enzyme capable of decomposing analyte to ammonia is urease.

7. The element of claim 6 wherein the urease is contained in the spreading layer and this layer is buffered to a pH of between about 4.5 and about 9.5.

8. An element for the determination of nitrogen-containing analyte in an aqueous sample, said element comprising at least one enzyme which catalyzes the decomposition of the analyte to $NH_3$, a $\beta$-diketone and a formaldehyde source or formaldehyde.

9. A composition for the detection of nitrogen-containing analyte in an aqueous sample, said composition comprising at least one enzyme which catalyzes the decomposition of the analyte to ammonia, a $\beta$-diketone capable of forming a detectable dihydropyridine on condensation with ammonia in the presence, and formaldehyde or a formaldehyde source.

10. The composition of claim 9 wherein the $\beta$-diketone is selected from the group consisting of:
(a) compounds of the formula

wherein R is an aryl group having from about 6 to about 20 carbon atoms, a straight- or branched-chain alkyl, alkoxy, or aralkyl group having from about 1 to about 20 carbon atoms, a cycloalkyl group of about 5 to about 7 carbon atoms or the atoms necessary to complete a recurring unit in a polymer backbone and $R^1$ is alkyl, cycloalkyl, or aryl; and
(b) polymers comprising:
(I) from about 1 to about 100% by weight of a polymerized monomer having the formula:

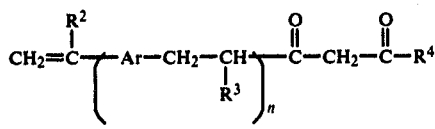

wherein n=0 or 1, $R^2$ is hydrogen or methyl, $R^3$ is hydrogen, alkyl, aryl or cycloalkyl, Ar is arylene, $R^4$ is alkyl or aryl; and
(II) from about 0 to about 99% by weight of at least one ethylenically unsaturated monomer.

11. The composition of claim 9 comprising from about 0.5 to about 5 weight percent of a formaldehyde source.

12. The composition of claim 9 comprising from about 1 to about 3 weight percent of a formaldehyde source.

13. The composition of claim 9 comprising from about 0.5 to about 5 weight percent of the β-diketone.

14. The composition of claim 9 comprising from about 1 to about 3 weight percent of the β-diketone.

15. The composition of claim 9, further comprising a buffer.

16. The composition of claim 15 wherein the buffer maintains the pH of the assay composition at from about 7.5 to about 9.5.

17. The composition of claim 15 wherein the buffer maintains the pH of the assay composition at from about 8.3 to about 8.8.

18. The composition of claim 15 wherein the buffer maintains the pH of the assay composition at from about 4.5 to about 6.5.

19. The composition of claim 15 wherein the buffer maintains the pH of the assay composition at from about 5.9 to about 6.2.

20. The composition of claim 9 wherein the formaldehyde source is selected from the group consisting of tetrahydrooxazoles, and 2-(hydroxymethyl)-2-nitro-1,3-propanediol.

21. The composition of claim 20 comprising from about 0.5 to about 5 weight percent of the formaldehyde source.

22. The composition of claim 20 comprising from about 1 to about 3 weight percent of the formaldehyde source.

23. The composition of claim 9 wherein the enzyme is urease.

24. A composition for the detection of urea in an aqueous sample comprising urease, a β-diketone and formaldehyde or a formaldehyde source.

25. The composition of claim 24 wherein the 62-diketone is selected from the group consisting of:
(a) compounds of the formula

wherein R is an aryl group having from about 6 to about 20 carbon atoms, a straight- or branched-chain alkyl, or aralkyl group having up to about 20 carbon atoms, a cycloalkyl group of about 5 to about 7 carbon atoms or the atoms necessary to complete a recurring unit in a polymer backbone and $R^1$ is alkyl, cycloalkyl, or aryl; and
(b) polymers comprising:
(I) from about 1 to about 100% by weight of a polymerized monomer having the formula:

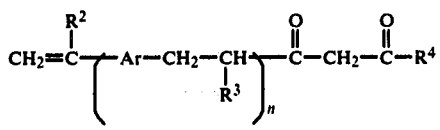

wherein n=0 or 1, $R^2$ is hydrogen or methyl, $R^3$ is hydrogen, alkyl, aryl or cycloalkyl, Ar is arylene, $R^4$ is alkyl or aryl; and
(II) from about 0 to about 99% by weight of at least one ethylenically unsaturated monomer.

26. The composition of claim 24 wherein the formaldehyde source is selected from the group consisting of tetrahydroxazoles, and 2-(hydroxymethyl)-2-nitro-1,3-propanediol.

27. The composition of claim 24 further including a buffer which maintains the pH of the composition at between about 4.5 to about 6.5.

28. A method for the detection of nitrogen-containing analyte capable of releasing ammonia upon enzymatic action, comprising the steps:
(a) contacting in an aqueous medium an aqueous sample suspected of containing such analyte and an assay composition comprising at least one enzyme which catalyzes the decomposition of the analyte to ammonia, a β-diketone and formaldehyde or a formaldehyde source; and
(b) detecting any color or fluorescence produced by dihydropyridine formed.

29. The method of claim 28 wherein the β-diketone is selected from the group consisting of:
(a) compounds of the formula

wherein R is an aryl group having from about 6 to about 20 carbon atoms, a straight- or branched-chain alkyl, alkoxy, or aralkyl group having up to about 20 carbon atoms, a cycloalkyl group of about 5 to about 7 carbon atoms or the atoms necessary to complete a recurring unit in a polymer backbone and $R^1$ is alkyl, cycloalkyl, or aryl; and
(b) polymers comprising:
(I) from about 1 to about 100% by weight of a polymerized monomer having the formula:

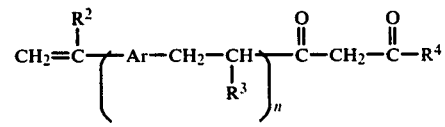

wherein n=0 or 1, $R^2$ is hydrogen or methyl, $R^3$ is hydrogen, alkyl, aryl or cycloalkyl, Ar is arylene, $R^4$ is alkyl or aryl; and
(II) from about 0 to about 99% by weight of at least one ethylenically unsaturated monomer.

30. The method of claim 28 wherein the composition comprises from about 0.5 to about 5 weight percent of a formaldehyde source.

31. The method of claim 28 wherein the composition comprises from about 1 to about 3 weight percent of a formaldehyde source.

32. The method of claim 28 wherein the composition comprises from about 0.5 to about 5 weight percent of the β-diketone.

33. The method of claim 28 wherein the composition comprises from about 1 to about 3 weight percent of the β-diketone.

34. The method of claim 28 wherein the composition further comprises a buffer.

35. The method of claim 34 wherein the buffer maintains the pH of the assay composition at from about 7.5 to about 9.5.

36. The method of claim 34 wherein the buffer maintains the pH of the assay composition at from about 8.3 to about 8.8.

37. The method of claim 34 wherein the buffer maintains the pH of the assay composition at from about 4.5 to about 6.5.

38. The method of claim 34 wherein the buffer maintains the pH of the assay composition at from about 5.9 to about 6.2.

39. The method of claim 28 wherein the formaldehyde source is selected from the group consisting of tetrahydrooxazoles, and 2-(hydroxymethyl)-2-nitro-1,3-propanediol.

40. The method of claim 39 wherein the composition comprises about 0.5 to about 5 weight percent of the formaldehyde source.

41. The method of claim 39 wherein the composition comprises from about 1 to about 3 weight percent of the formaldehyde source.

42. The method of claim 28 wherein the enzyme is urease.

43. A method for the detection of urea comprising the steps of
(a) contacting in an aqueous medium a sample suspected of containing urea and an assay composition comprising urease, a β-diketone selected from the group consisting of compounds of the formula

R—CO—CH$_2$—CO—CH$_3$ wherein R is an aryl group having from about 6 to about 20 carbon atoms, a straight- or branched-chain alkyl, alkoxy, or aralkyl group having up to about 20 carbon atoms, a cycloalkyl group of about 5 to about 7 carbon atoms or the atoms necessary to complete a recurring unit in a polymer backbone, and formaldehyde or a formaldehyde source; and
(b) measuring any color or fluorescence produced.

44. The method of claim 43 wherein the formaldehyde source is selected from the group consisting of tetrahydrooxazoles, and 2-(hydroxymethyl)-2-nitro-1,3-propanediol.

45. The method of claim 43 wherein the assay composition also includes a buffer which maintains the pH of the aqueous medium at between about 4.5 and about 6.5.

46. The method of claim 43, wherein the assay composition also includes a buffer which maintains the pH of the aqueous medium at between about 8.3 and 8.8.

47. The method of claim 43 wherein the sample for analysis and the assay composition are contacted at a temperature of between about 37° C. and about 60° C. for a period of up to about 5 minutes.

* * * * *

UNITED STATES PATENT AND TRADEMARK OFFICE
CERTIFICATE OF CORRECTION

PATENT NO. : 4,194,063
DATED : March 18, 1980
INVENTOR(S) : David S. Frank and Ignazio S. Ponticello It is certified that error appears in the above-identified patent and that said Letters Patent are hereby corrected as shown below:

Column 21, lines 58-59, "62-diketone" should read ---β-diketone---.

Signed and Sealed this

Seventeenth Day of June 1980

[SEAL]

Attest:

SIDNEY A. DIAMOND

Attesting Officer

Commissioner of Patents and Trademarks